United States Patent [19]

Pugh et al.

[11] Patent Number: 5,766,669

[45] Date of Patent: Jun. 16, 1998

[54] SINTERING PROCESS FOR PRODUCING THIN FILMS OF CALCIUM PHOSPHATE ENTITIES

[75] Inventors: Sydney M. Pugh, Glenburnie; Timothy J. N. Smith, Kingston, both of Canada

[73] Assignee: Millenium Biologix Inc., Ontario, Canada

[21] Appl. No.: 960,702

[22] Filed: Oct. 30, 1997

Related U.S. Application Data

[63] Continuation of Ser. No. 519,057, Aug. 24, 1995, abandoned.

[51] Int. Cl.$^6$ .................................. B05D 3/02; B05D 5/00
[52] U.S. Cl. ....................... 427/2.27; 427/2.11; 427/2.12; 427/376.1
[58] Field of Search ................. 427/2.27, 376.1, 427/2.11, 2.12

[56] References Cited

U.S. PATENT DOCUMENTS

| | | | |
|---|---|---|---|
| 4,871,578 | 10/1989 | Adam et al. | 427/2.27 |
| 4,983,182 | 1/1991 | Kijima et al. | 427/2.27 |
| 4,988,362 | 1/1991 | Toriyama et al. | 427/2.27 |
| 4,990,163 | 2/1991 | Ducheyne et al. | 427/2.27 |
| 5,030,474 | 7/1991 | Saito et al. | 427/2.27 |
| 5,077,079 | 12/1991 | Kawamura et al. | 427/2.27 |
| 5,128,169 | 7/1992 | Saita et al. | 427/2.27 |
| 5,141,576 | 8/1992 | Shimamune et al. | 427/2.27 |
| 5,266,248 | 11/1993 | Ohtsuka et al. | 427/2.27 |

FOREIGN PATENT DOCUMENTS

WO9426872  11/1994  WIPO.

OTHER PUBLICATIONS

"The effect of substrate composition and condition on resorption by isolated osteoclasts", Bone and Mineral, 6 (1989), pp. 261–275, Shimizu, et al. (no month).

"An Assay System Utilizing Devitalized Bone for Assessment of Differentiation of Osteoclast Progenitors", Journal of Bone and Mineral Research, vol. 7, No. 3, 1992, pp. 321–328, Amano, et al. (Mar.).

"Resorption Of Bone By Isolated Rabbit Osteoclasts", J. Cell. Sci. 66, 1984, pp. 383–399, Chambers, et al. (no month available).

"Failure of Cells of the Mononuclear Phagocyte Series to Resorb Bone", Calcif Tissue Int. (1984) 36, pp. 556–558, Chambers, et al. (no month).

"The resorption of biological and non-biological substrates by cultured avian and mammalian osteoclasts", Ana. Embryo (1984) 170, pp. 247–256, Jones, et al. (no month).

"Resorption of Dentine by Isolated Osteoclasts in vitro", Br. Dent J.1984, pp. 216–219, Boyde, et al. (no month available).

*Primary Examiner*—Diana Dudash
*Attorney, Agent, or Firm*—Bell Seltzer Intellectual Property Law Group Alston & Bird LLP

[57] ABSTRACT

An improved process for producing a thin film of calcium phosphate entities to support bone cell activity thereon. The material to be sintered is prepared by combining a solution of ammonium phosphate with a solution of calcium nitrate to form a sol-gel containing hydroxyapatite. A film of the sol gel is applied to at least one side of the substrate and the film coated on the substrate is sintered to form a solid film of calcium phosphate entities. The improvement in the process comprising sintering the film at temperatures selected from a range of temperatures which optimize a composition of calcium phosphate entities in the film. The sintering step converts hydroxyapatite to $\alpha$-tricalcium phosphate where extent of such conversion is temperature dependent. The optimized composition comprises a ratio of hydroxyapatite to $\alpha$-tricalcium phosphate in the range of 50:50 to 20:80. A sintering temperature is selected to provide these ratios. The sintering temperature is selected from a range of 920° C. up to 1100° C. where the higher the select temperature, the greater the amount of $\alpha$-tricalcium phosphate in the ratio.

1 Claim, No Drawings

SINTERING PROCESS FOR PRODUCING THIN FILMS OF CALCIUM PHOSPHATE ENTITIES

This application is a continuation, of copending application Ser. No. 08/519,057, filed Aug. 24, 1995, now abandoned.

FIELD OF THE INVENTION

This invention relates to an improved process for producing tin films of calcium phosphate entities to support bone cell activity thereon The thin film comprises an optimum composition of hydroxyapatite to α-tricalcium phosphate having ratios in the range of 50:50 to 20:80.

Bone is a complex mineralizing system composed of an inorganic or mineral phase, an organic matrix phase, and water. The inorganic mineral phase is composed of crystaline calcium phosphate salts while the organic matrix phase consists mostly of collagen and other noncollagenous proteins. Calcification of bone depends on the close association between the organic and inorganic phases to produce a mineralized tissue.

The process of bone growth is regulated to meet both structural and mechanical stresses. The cells involved in the processes of bone formation, maintenance, and resorption are osteoblasts, osteocytes, and osteoclasts. Osteoblasts synthesize the organic matrix, osteoid, of bone which after calcium phosphate crystal growth and collagen assembly becomes mineralized. Osteocytes regulate the flux of calcium and phosphate between the bone mineral and the extracellular fluid. Osteoclasts function to resorb bone and are essential in the process of bone remodelling Disturbing the natural balance of bone formation and resorption leads to various bone disorders. Increased osteoclast activity has been demonstrated to lead to bone disease characterized by a decrease in bone density such as that seen in osteoporosis, osteitis fibrosa and in Paget's disease. All of these diseases are a result of increased bone resorption In order to understand the mechanisms involved which regulate bone cell functioning, it is important to be able to assess the normal function of bone cells and also the degree of perturbation of this activity in various bone diseases. This will lead to the identification of drugs targeted to restore abnormal bone cell activity back to within normal levels.

Several research groups have developed methods to directly observe the activity of isolated osteoclasts in vitro. Osteoclasts, isolated from bone marrow cell populations, have been cultured on thin slices of natural materials such as sperm whale dentine (Boyde et al Brit Dent J. 156, 216, 1984) or bone (Chambers et al J. Cell Sci. 66, 383, 1984). The latter group have been able to show that this resorptive activity is not possessed by other cells of the mononuclear phagocyte series (Chambers & Horton, Calcif Tissue Int 36, 556, 1984). More recent attempts to use other cell culture techniques to study osteoclast lineage have still had to rely on the use of cortical bone slices (Amano et al. and Kerbyiet al J. Bone & Min Res. 7(3)) for which the quantitation of resorptive activity relies upon either two dimensional analysis of resorption pit areas of variable depth or stereo mapping of the resorption volume. Such techniques provide at best an accuracy of approximately 50% when assessing resorption of relatively thick substrata In addition these analysis techniques are also very time consuming and require highly specialized equipment and training. Furthermore, the preparation and subsequent examination of bone or dentine slices is neither an easy nor practical method for the assessment of osteoclast activity.

The use of artificial calcium phosphate preparations as substrata for osteoclast cultures has also met with little success. Jones et al (Anat Embryol 170, 247, 1984) reported that osteoclasts resorb synthetic apatites in vitro but failed to provide experimental evidence to support this observation. Shimizu et al (Bone and Mineral 6, 261, 1989) have reported that isolated osteoclasts resorb only devitalized bone surfaces and not synthetic calcium hydroxyapatite. These results would indicate that functional osterclasts are difficult to culture in vitro.

The assignee of the applicants has a international PCT patent application WO94/26872 describing a sintering process for forming thin films of calcium phosphate entities on which bone cell function occurs. This is believed to be the first thin layer of synthetic material on which osteoclasts can exhibit extended activity. As described in that application, a variety of factors should be considered in providing in the thin film the desired ratio of hydroxyapatite to tricalcium phosphate. Such parameters include:

1) amounts of reagents for preparing the sol-gel containing hydroxyapatite;
2) rate of combination of reagents;
3) duration and rate of mixing when making the sol- gel;
4) rates and methods of precipitation and separation;
5) process environmental conditions during the manufacture of the sol-gel;
6) velocity of removal of the substrate from the sol-gel in dip coating a film thereon;
7) sintering temperature;
8) sintering in a controlled atmosphere such as inert gas, a vacuum or an atmosphere with water vapour present It was therefore suggested in the earlier PCT patent application, that in order to obtain a broad range in ratios of hydroxyapatite to tricalcium phosphate, many of these parameters need to be considered in order to achieve the ratios of 10:90 through to 90:10. The suggested sintering temperatures in an air atmosphere were from approximately 800° C. to approximately 1100°. It was established that at 800° C. the film was predominantly hydroxyapatite, that is a ratio of approximately 90:10. A sintering temperature of about 900° C. provided ratios of about 70:30. At 1000° C., the ratio was about 10:90 and at 1100° C. the film was predominantly tricalcium phosphate. It was also suggested that sintering in a vacuum at a 1000° C. produced a ratio of approximately 66:34. It has now been found that the preferred ratios are from 50:50 to 20:80. The optimum ratio is approximately 333:666. To achieve these ratios, consideration can be given to several of the above factors. However, it is desirable to minimize the variability in several of the above factors and achieve the desired ratios for optimum film compositions in an exacting s reproducible manner.

Applicants have now found that formation of the sol- gel, in accordance with the standard technique described applicants published PCT application WO94/26872 in combination with discovered exacting sintering temperatures can achieve selected desired ratios of the above identified optimized range.

SUMMARY OF THE INVENTION

In accordance with an aspect of the invention, a process for producing a thin film of calcium phosphate entities to support bone cell activity thereon where the thin film is provided on a substrate, includes the steps of:

i) preparing a sol-gel by combining a solution of ammonium phosphate with a solution of calcium nitrate to form a sol-gel containing hydroxyapatite;

ii) applying to at least one side of the substrate a film of the sol-gel;

iii) sintering the film coated on the substrate to form a solid film of the calcium phosphate entities;

the improvement comprising:

iv) sintering the film at temperatures selected from a range of temperatures which optimize a composition of calcium phosphate entities in the film, the sintering step converting hydroxyapatite of the film to α-tricalcium phosphate where extent of such conversion is temperature dependent;

v) the optimized composition comprises a ratio of hydroxyapatite to α-tricalcium phosphate in the range of 50:50 to 20:80; and vi) selecting a sintering temperature from the range of 920° C. up to 1100° C. where sintering temperature is selected at higher levels to produce ratios which are closer to the upper conversion ratio of 20:80.

In accordance with another aspect of the invention, selected sintering temperatures between 920° C. to 950° C. produce a ratio in the range of 50:50 to 333:666.

In accordance with another aspect of the invention, selected sintering temperatures between 1000° C. to 1100° C. to produce a ratio in the range of 333:666 to 20:80.

In accordance with another aspect of the invention, in order to produce a ratio of approximately 333:666, sintering temperature is between 950° C. to 1000° C. and preferably approximately 975° C.

DETAILED DESCRIPTION OF THE PREFERRED EMBODIMENTS

A significant improvement is provided by this invention to produce on a consistent basis thin film of calcium phosphate entities which are within the desired range of 50:50 to 20:80. We have found that ratios which include less than 20% hydroxyapatite are not stable due to dissolution problems with the higher presence of α-tricalcium phosphate. Above approximately 50% by weight hydroxyapatite, although the film is stable, the resorption performance in respect of assayed normal osteoclast activity becomes less reliable. From the standpoint of bone cell activity, the optimum ratio is 333:666 but based on extensive observation of bone cell activity, the acceptable range for the ratio is from 50:50 through to 20:80. Applicants have surprisingly discovered that by using the standard sol-gel manufacture technique described in published application WO94/26872 and carrying out sintering at specific temperatures, the desired ratios can be achieved where such ratios were achieved in accordance with the published application, but variation in sintering conditions and other parameters affected reproducibility of that process.

In order to further facilitate an understanding of this invention, reference may be made to published PCT application WO94/26872, the subject matter of which is herein incorporated by reference. Before describing in detail the improved aspects of the invention, it is important that various background aspects of the thin film be described.

The thin film as provided on a suitable support, in accordance with this invention, significantly advances the study and understanding of bone cell functional properties. The make-up of the film, as provided in accordance with this invention, permits the culture of various types of bone cells thereon. The surface make-up may be adjusted to encourage a significant degree of resorption of the calcium phosphate entities of the film material through to a negligible degree of resorption of the calcium phosphate entities in the study of osteoclast activity. Similarly, osteoblast activity may be studied by detecting a build up of bone-like material. The ability to provide the material in a film which is sufficiently thin that resorption of the entities by osteoclasts can be detected by the disappearance of resorbed calcium phosphate entities provides a simple inexpensive format for analysis compared to the prior art techniques. The film make-up as made in accordance with this invention, supports the biological function of bone cells. The benefit in providing the film on a transparent supporting substrate, such as quart or glass, lends to easy evaluation techniques of the diagnostic process.

Ideally the film thickness is greater than 0.1 micron because it has been found that at film thicknesses less than 0.1 microns it is difficult to obtain uniform film coverage, free from discrete voids. As to the upper thickness limit for the film, it can be of any desired thickness depending upon its end use. As will be discussed, the degree of resorption may be detected by light transmittance, which preferably requires a film less than 10 microns in thickness. Preferably the substrate is of quartz or some other thermally tolerant material because of the required sintering of the film once applied to the substrate. Other materials include metals, polymers or ceramic materials other than the film material. Glass may be used when the film material is sintered by use of a surface sintering device which heats the glass surface to a very high temperature for a brief period of time to achieve the degree of sintering necessary in providing the desired type of film. Quartz readily withstands these temperatures and has the desired degree of transparency to permit light transmittance tests to determine the extent of resorption of calcium phosphate entities from the film material.

The developed thin films may be used in kits and the like to provide for assessment of bone cell activity. The film may be embodied in the form of a "kit" comprising quartz substrates, (or other suitable transparent support) precoated with an adherent calcium phosphate thin film, which may be used in a cell culture vessel (possibly a 24-well optionally sterilized multi-well plate i.e. of approximately 15 mm diameter) as a system suitable for the culture of mixed bone cell populations. The device is simple and relies on only routine laboratory equipment and techniques for use, is suitable for quantitative analysis, and is inexpensive to fabricate but strong enough to withstand normal levels of handling and may be packaged in lots, of (for example) 24 samples in a plastic presentation box The thin film surfaces have a defined and reproducible chemistry and are mechanically strong enough to withstand transport when used with an appropriate packing material.

Modifications of the device could be designed for specific applications. For example, each substrate could be presented in a plastic support ring. The latter could be employed not only as a packaging spacer, and thus be sterilized with the substrate, but also a lip to prevent spread of culture medium and cells from the substrate itself and thus facilitate quantification of the resorptive activity. Such protection rings could also be used as stacking devices to enable multiple substrates to be employed simultaneously in the same culture well. The latter could then be enclosed in a sealed culture vessel supplied with circulating medium and could also be adopted for low and zero gravitational environments.

In each case the culture conditions may be such that osteoclasts, in either mononuclear or multinucleate form could be expected to survive in a functional state and resorb the artificial calcium phosphate of the film.

These substrates may be used to assess the resorptive activity of osteoclasts and monitor the change in this level of resorptive activity either as a result of a disease process or the inclusion, in the culture medium, of an agent such as a drug which would influence, either directly or indirectly, osterclastic resorptive activity.

The device may be used as a means of quantifying the resorptive activity of osteoclasts or build-up of bone-like material by activity of osteoblasts. Such activity analysis may occur under continuous real-time monitoring, time-lapse intervals or end-point determination. The steps in establishing osteoclast activity are common to each of the above monitoring schedules in that bone cells (either animal or human) are cultured, in specific conditions, on one or more of the devices. The culture period is from several hours to many days and preferably from approximately 2 to 10 days (the optimum time is cell species and protocol dependent), during which time the extent of osteoclast activity may be continuously monitored, periodically monitored, or simply not monitored on an on-going basis in favour of final-end-point determination. Similarly, osteoblast activity may be observed by determining extent of bone-like material build-up.

Although the provision of pure or essentially pure hydroxyapatite was understood to be the calcium phosphate entity of choice in making the film, we have determined that films which are predominantly of hydroxyapatite do not encourage normal function of osteoclasts and osteoblasts, and, in actual fact, in the presence of osteoclasts, very little activity can be observed. It has been found, however, that by providing a mixture of calcium phosphate entities which include hydroxyapatite and α-tricalcium phosphate, the degree of resorption is encouraged through a broad range where the film predominantly of α-tricalcium phosphate provides the highest degree of resorption, whereas a film predominantly of hydroxyapatite provides a negligible degree of resorption. It is this realization, in accordance with this invention, with respect to the presence of α-tricalcium phosphate that explains the failure of other calcium phosphate films to encourage functional properties in osteoclasts being cultured on the films. This aspect, in combination with the other aspect of the invention in providing a thin film which permits, for example, transmittance of light or light reflection, allows one to carry out diagnostic procedures to evaluate several functional properties of bone cells being cultured on the films in accordance with this invention.

Surprisingly, it has been found that standardizing the preparation of the sol-gel and selecting a very specific range of sintering temperatures, not only achieves the desired ratios but also reveals that the optimum composition is formed by conversion of hydroxyapatite as prepared by the sol-gel process to α-tricalcium phosphate. Little or no β-tricalcium phosphates have been detected in these preferred optimized film compositions. There is no need to prepare a sol-gel which is a combination of hydroxyapatite and α-tricalcium phosphate. Instead, the technique as described in published PCT application WO 94/26872 is sufficient in preparing a sol-gel of hydroxyapatite. The chemical reaction for making hydroxyapatite in a medium of elevated pH is as follows:

$$5Ca(NO_3)_2 + 3NH_4H_2PO_4 + 7HN_4OH$$
$$\rightarrow Ca_5(PO_4)_3 + 10NH_4NO_3 + 6H_2O$$

The hydroxyapatite is stable in neutral and/or alkaline media. Preferably the reaction medium is brought to an elevated pH usually in the range of about 12. The phosphate solution is added drop by drop into the calcium solution to prevent the formation of tetracalcium monohydrogen triphosphate thereby obtaining a homogenous product of the desired hydroxyapatite.

Once the sol-gel is prepared, it may be applied as a thin film to the substrate in a variety of techniques. For example, the dip-coating method (C. J. Brinker et al., Fundamentals of Sol-Gel Dip Coating, Thin Solid Films, Vol. 201, No. 1, 97–108, 1991) consists of a series of processes: withdrawal of the substrate from a sol or solution at a constant speed, drying the coated liquid film at a suitable temperature, and firing the film to a final ceramic.

In spin-coating the sol-gel is dropped on a plate which is rotating at a speed sufficient to distribute the solution uniformly by centrifugal action. Subsequent treatments are the same as those of dip coating.

It is appreciated that there are a variety of other techniques which may be used to apply a thin film of the sol-gel to the substrate. Other techniques include a spraying of the sol-gel roller application of the sol-gel spreading of the sol-gel and painting of the sol-gel.

An alternative to coating discrete discs of a singular size is to coat an enlarged substrate with a film of the sol-gel. The entire film on the substrate is then sintered. A device, such as a grid, may then be applied over the film to divide it into a plurality of discrete test zones. An improvement on this arrangement is described in applicant's co-pending U.S. application entitled "Multi-Well Bone Cell Culture Device for Use in Assessment of Bone Cell Activity", Ser. No. 08/518,912, filed Aug. 24, 1995, now abandoned.

In these various techniques of the sol-gel application, the thickness and quality (porosity, microstructure, crystaline state and uniformity) of formed films are affected by many factors. These include the physical properties, composition and concentration of the starting sot the cleanliness of the substrate surface, withdrawal speed of the substrate and the firing temperature. In general the thickness depends mainly on the withdrawal rate and sol viscosity for a dip coating process. Since heterogeneity in the sol is responsible for the formation of macropores and cracks, the coating operation should be undertaken in a clean room to avoid contamination of the sol. At the heat-treatment stage, high temperatures are required to develop the required microstructure.

The purpose of applying the dip coating method to fabricate calcium phosphate films is threefold: (a) to make films with required qualities (uniformity, thickness, porosity, etc.) and (b) to make translucent calcium phosphate films on transparent substrates for biological experiments.

It has been surprisingly found that sintering of the dried film of hydroxyapatite may be carried out in a standard type of high temperature oven without any need to control the atmosphere in the oven When a new oven is used or an oven contaminated by previous use for other purposes, it is preferred to cycle the oven through the sintering temperature range several times while the oven is empty. Such pre-conditioning of the oven removes any volatiles and prepares it for use. No additional steps are required. Ambient air may be present in the oven during the break-in period and during normal use for sintering coated substrates where the presence of ambient air does not hamper the process and results in producing consistent results for the desired ratio. Under these conditions, the sintering temperature may range from 920° C. up to 1100° C. in providing the desired ratios of 50:50 up to 20:80. It has been found that as the temperature increases, the conversion of hydroxyapatite into α-tricalcium phosphate is also increased. At sintering temperatures in the range of 920° C. up to 950° C. the ratio may vary from 50:50 towards 333:666. At selected sintering temperatures in the range of 950° C. to 10000 the ratio is approximately 333:666. Increasing the temperature beyond a 1000° C. and up to 1100° C. further increases the conversion and produces compositions having ratios in the range of 333:666 to 20:80.

The preferred sintering temperature is approximately 975° C. where the ratio of 333:666 is achieved.

The following procedures exemplify preferred embodiments of the invention for achieving the desired optimum composition for the sintered thin film.

PROCEDURE 1

The following procedure is based on preparing sufficient sol-gel to coat a limited number of substrate discs. As per the above-noted chemical reaction, Solution A comprises a calcium nitrate which is preferably calcium nitrate tetrahydrate. Solution B comprises an ammonium phosphate which is preferably ammonium dihydrogen orthophosphate (mono basic). Solution A is mixed with Solution B to produce the desired sol-gel Solution C. Solution A is prepared by adding 40 mls of doubly distilled water to 4.722 grams of calcium nitrate—Ca(NO$_3$)2. The solution is stirred at moderate speed for sufficient time to dissolve al of the calcium nitrate which is normally in the range of 3 minutes. To this solution, 3 mls of ammonia hydroxide (NH$_4$OH) is added and stirred for approximately another 3 minutes. The pH of the solution is tested where a pH of about 12 is desired. To this solution is added 37 mls of double distilled water to provide a total solution volume of approximately 80 mls. The solution is stirred for another 7 minutes and covered.

Solution B is prepared by adding 60 mls of double distilled water to a 250 ml beaker containing 1.382 grams of NH$_4$H$_2$PO$_4$. The beaker is covered and stirred at moderate speed for 3 to 4 minutes until all NH$_4$H2PO$_4$ is dissolved. To this solution is added 71 mls of NH$_4$OH and the beaker then covered and stirring continued for approximately another 7 minutes. The pH of the solution is tested where a pH of about 12 is desired. To this is added another 61 mls of double distilled water and the beaker covered to provide a total solution volume of approximately 192 mls. The solution is then stirred for a further 7 minutes and covered.

The desired sol-gel is then prepared by combining Solution B with Solution A. AU of Solution A is introduced to a 500 ml reagent bottle. Stirring is commenced at a moderate speed and Solution B introduced to the reagent bottle at a rate of approximately 256 mls per hour until all 192 ml of Solution B is delivered into Solution A. An excess of Solution B may be used to compensate for any solution which may remain in the 250 ml beaker or any tubing used in the transfer process. After completion of this addition and combination of Solution A with Solution B, the resultant Solution is stirred at moderate speed for approximately 23 to 24 hours. The resultant sol-gel is inspected for any abnormal precipitation or agglomeration If any abnormal precipitation or agglomeration has occurred, the solution must be discarded and preparation commenced again The sol is then carefully transferred to another 500 ml reagent bottle so as to avoid any inclusion of particle agglomerations that may be present on the walls of the original reagent bottle. Approximately 240 mls of Solution C, that is the resultant sot is delivered to a centrifuge bottle and centrifuged for 20 minutes at about 500 rpm at room temperature. Following centrifugation, 180 mls of supernatant is discarded without disturbing the sediments. The sediments are gently resuspended by mixing in a smooth rotating manner for about 30 minutes. Viscosity of the sol is then measured and preferably is between 20 to 60 cP. The sol is then ready for dip coating of the selected substrate.

PROCEDURE 2

Cleaning of quartz disc as one preferred substrate—the discs are placed in a glass beaker and chromic acid cleaning solution is supplied to the glass beaker to cover all discs. The beaker is then covered. The discs are then sonicated in a water bath for 1 hour. The acid is washed away using tap water for 20 minutes. The residual tap water is removed by three changes of doubly distilled water. After the final change of double distilled water, every single disc is dried with lint-free towel and inspected for flaws in the quartz surface. Any residual particulate on the surface is removed as needed with compressed nitrogen or air. The discs are stored in covered trays in an aseptic environment

PROCEDURE 3

The quartz disc substrate as one preferred substrate is dipped in the sol prepared by Procedure 1. The disc is grasped in a manner to avoid touching the surface. The disc is dipped in the sol, preferably by machine. The disc is removed from the sol at a prescribed withdrawing velocity. The coating on one side of the disc is removed. The coated substrate is then placed in a clean petri dish and covered and dried at room temperature. The film, as formed prior to sintering, should be uniform without cracks, clumps or voids. It is understood that the dip coating process as applied to a face of a disc, may also be applied to any other shape of substrate, such as, a flat rectangular shaped substrate of quartz.

PROCEDURE 4

The following sintering process may be carried out in standard laboratory furnaces of various sizes, capable of operating at temperatures from ambient up to at least 1100° C., and designed to maintain accurate and stable Internal temperatures, particularly between 800° C. and 1100° C., such as Lindberg models 51744 or 894-Blue M. The coated substrates as prepared by Procedure 3 are carefully transferred onto a standard ceramic plate (as is common practice in the Lindberg oven)—using, for example tweezers to avoid touching the coated surface. The ceramic plate is used as a carrier during the sintering process to filtrate easy loading and withdrawal of multiple substrates from the furnace. The furnace temperature is set to the temperature required to achieve the desired ratios of HA:α TCP. Utilizing a programmable furnace such as the Indberg model 894-Blue M, the furnace may be programmed to hold the desired temperature, which will normally be selected from the range 920° C. to 1100° C., for times not typically exceeding one hour. In the case of non-programmable furnaces, a separate timer may be used to warn the operator to tun the furnace off at the end of the required sintering time at selected temperature. The furnace is turned on and as it is heating to the required operating temperature, the ceramic plate carrying the substrates is loaded at the point when the furnace approaches sintering temperatures for example 800° C. The furnace door is shut again immediately afterwards. The furnace is then allowed to reach the selected operating temperature for the required time and then turned off either automatically or manually. The ceramic plate carrying the sintered substrates is removed at any time after the internal furnace temperature has cooled to an acceptable and safe touch-temperature of approximately 60° C. Individual substrates may then be stored or packaged for final use.

In accordance with this improved process, thin films of hydroxyapatite/α-tricalcium phosphate can be produced on a consistent basis having the desired composition where variability in the various processing parameters have been minimized to ensure such consistency.

Although preferred embodiments of the invention are described herein in detail, it will be understood by those skilled in the art that variations may be made thereto without departing from the spirit of the invention or the scope of appended claims.

We claim:

1. In a process for producing a thin film of calcium phosphate entities to support bone cell activity thereon where said thin film is provided on a substrate, said process including the steps of:

i) preparing a sol-gel by combining a solution of ammonium phosphate with a solution of calcium nitrate to form a sol-gel containing hydroxyapatite;

ii) applying to at least one side of said substrate a film of said sol-gel;

iii) sintering said film coated on said substrate to form a solid film of said calcium phosphate entities;

the improvement comprising:

iv) sintering said film at a temperature ranging from 950° C. to 1000° C. in ambient air to optimize the composition of calcium phosphate entities in said film, said sintering step converting hydroxyapatite to α-tricalcium phosphate in a ratio of approximately 333:666 of hydroxyapatite to α-tricalcium phosphate.

* * * * *